United States Patent
Spickermann

[11] Patent Number: 6,066,261
[45] Date of Patent: May 23, 2000

[54] METHOD OF MONITORING PART OF A BLOOD TREATMENT MACHINE AND A BLOOD TREATMENT MACHINE WITH A MONITORING DEVICE

[75] Inventor: Reiner Spickermann, Burghausen, Germany

[73] Assignee: Fresenius Medical Care Deutschland GmbH, Bad Homburg v.d.H., Germany

[21] Appl. No.: 09/219,045

[22] Filed: Dec. 23, 1998

[30] Foreign Application Priority Data

Dec. 23, 1997 [DE] Germany ............... 197 57 523

[51] Int. Cl.[7] ............ B01D 61/32; B01D 61/28; B01D 65/10
[52] U.S. Cl. ............ 210/739; 210/85; 210/90; 210/97; 210/645; 210/646; 210/741
[58] Field of Search .................. 210/85, 90, 97, 210/645, 646, 739, 741

[56] References Cited

U.S. PATENT DOCUMENTS 4,444,596 4/1984 Gortz et al. ................... 210/90
5,674,404 10/1997 Kenley et al. ................ 210/741
5,711,883 1/1998 Folden et al. ................. 210/646
5,910,252 6/1999 Truitt et al. .................. 210/645

FOREIGN PATENT DOCUMENTS 39 23 078 9/1990 Germany .
42 39 937 6/1994 Germany .

*Primary Examiner*—John Kim
*Attorney, Agent, or Firm*—Kenyon & Kenyon

[57] ABSTRACT

To monitor the functionality of a partial device of a blood treatment machine, an excess pressure is built up on the blood side and on the dialysis fluid side and is monitored to detect a pressure drop. To do so, the flow path through the dialysis fluid inlet line (12), the dialysis fluid outlet line (13) and the blood outlet line (6) can be interrupted, and the blood pump (7) is started. The test pressure on the dialysis fluid side is built up due to the ultrafiltrate passing through the membrane (2) of the dialyzer (1). Any leakage in the closed volume, which includes a part of the blood path as well as part of the dialysis fluid path, is then detected by a (greater) pressure drop.

12 Claims, 1 Drawing Sheet

METHOD OF MONITORING PART OF A BLOOD TREATMENT MACHINE AND A BLOOD TREATMENT MACHINE WITH A MONITORING DEVICE

FIELD OF THE INVENTION

The present invention relates to a method of monitoring the functionality of a part of a blood treatment machine and a blood treatment machine with a device for monitoring the functionality of a part of the blood treatment machine.

BACKGROUND INFORMATION

Known hemodialysis machines have a control device which makes it possible to preselect a certain ultrafiltration rate. This device ensures that a predetermined quantity of ultrafiltrate is removed from the patient during the hemodialysis treatment, regardless of the viscosity of the blood to be treated and the properties of the dialyzer.

Since a defect in the device for monitoring the ultrafiltration can endanger the patient, safety standards require the presence of a safety system as a safeguard against ultrafiltration that would be hazardous for the patient. The most commonly used safety system monitors the transmembrane pressure for this purpose.

However, one result of the development of dialyzers with high permeability membranes, known as high-flux dialyzers, has been that an excessively high or low ultrafiltration rate which could endanger the patient cannot be detected with sufficient reliability by monitoring the transmembrane pressure.

German Patent Application No. 42 39 937 describes a method of determining the functionality of a partial device of a hemodialysis machine, where the dialyzer is separated from the dialysis fluid circuit for short periods of time at periodic intervals during dialysis, and the pressure profile in the dialysis fluid is determined by means of a pressure-holding test for deviation from the stable state. This method has proven successful in practice. However, a disadvantage of this is that the known method where the dialyzer is separated from the dialysis fluid circuit does not include the dialyzer in the testing. Thus defective O rings on the dialyzer couplings, which are a common cause of leakage, cannot be detected.

SUMMARY OF THE INVENTION

An object of the present invention is to provide a method of monitoring the functionality of a partial device of a blood treatment machine which includes both the blood path and the dialysis fluid path in testing.

The present invention provides a method of monitoring the functionality of a partial device of a blood treatment machine having:
a dialyzer (1) subdivided by a semipermeable membrane (2) into a first and a second chamber (3, 4),
a blood inlet line (5) connected to the inlet of the first chamber (3) of the dialyzer (1) and to a blood pump (7), and a blood outlet line (6) connected to the outlet of the first chamber (3) of the dialyzer (1),
a dialysis fluid inlet line (12) leading from the dialysis fluid source (11) to the inlet of the second chamber (4) of the dialyzer (1) and a dialysis fluid outlet line (13) leading from the outlet of the second chamber (4) of the dialyzer (2) to a discharge point (14),
with the following process steps:
separating a section on the dialyzer end from the dialysis fluid inlet line (12) at a first separation point (c),
separating a section on the dialyzer end from the dialysis fluid outlet line (13) at a second separation point (d),
separating a section on the dialyzer end from the blood outlet line (6) at a third separation point (b),
separating a section on the dialyzer end from the blood inlet line (5) at a fourth separation point (a),
building up an excess pressure in the closed volume, which includes the dialyzer (1) and the sections of the dialysis fluid inlet and outlet lines on the dialyzer end between the first and second separation points and the blood inlet and outlet lines between the third and fourth separation points, and
monitoring the excess pressure to detect a pressure drop in the closed system.

In addition, an object of the present invention is to create a blood treatment machine with a device for monitoring the functionality of a partial device thereof, which includes the blood path as well as the dialysis fluid path in the testing.

The present invention thus also provides a blood treatment machine with a dialyzer (1) subdivided into a first and second chamber (3, 4) by a semipermeable membrane (2),
a blood inlet line (5) connected to the inlet of the first chamber (3) of the dialyzer (1) and to a blood pump (7), and a blood outlet line (6) connected to the outlet of the first chamber (3) of the dialyzer (1) and to a first shut-off device (8), and
a dialysis fluid inlet line (12) leading from a dialysis fluid source (11) to the inlet of the second chamber (4) of the dialyzer (1) and connected to a second shut-off device (15), and a dialysis fluid outlet line (13) leading from the outlet of the second chamber (4) of the dialyzer (1) to an outlet (14) and connected to a third shut-off device (16).

The machine is characterized by a device (17) for monitoring the functionality of a partial device thereof comprising a control device (18) designed so that the shut-off devices (8, 15, 16) can be actuated and the blood pump can be operated to build up an excess pressure in the closed volume consisting of the dialyzer (1) and the sections of the dialysis fluid inlet and outlet lines (12, 13) and the blood inlet and outlet lines (5, 6) on the dialyzer end, and a pressure-measuring device for detecting a pressure drop in the closed volume.

With the method according to the present invention and the device according to the present invention, an excess pressure is built up in part of the blood path and part of the dialysis fluid path and is monitored for detection of a pressure drop. The test pressure on the dialysis fluid side is built up due to ultrafiltrate passing through the membrane of the dialyzer. Any leakage in the closed system, including part of the blood path as well as part of the dialysis fluid path, is then detected by a (greater) pressure drop. Fault detection can be based on detection of a threshold value or on a curve analysis.

To build up the excess pressure, the flow path through the dialysis fluid inlet and outlet lines and the blood inlet and outlet lines is interrupted. If the blood pump is an occluding pump, the flow path through the blood inlet line is interrupted by the pump. Thus, separate shut-off devices need not be provided in the blood inlet line. Operation of the blood pump is then started to build up the excess pressure. Buildup of a sufficient test pressure can be monitored actively by a pressure sensor or by volume control by means of a fixed delivery rate by the blood pump. It is also possible for an adequate test pressure to be built up by stopping the running blood pump and separating the blood outlet line at the same time. The system pressure which is maintained in this way can then be used as the test pressure.

The amount of ultrafiltrate needed to generate the test pressure is typically about 10 mL. The total test time can be kept below one minute with the known high-flow dialyzers, so cyclic operation at predetermined intervals, for example, is possible during the blood treatment. However, the pressure-holding test can also be performed before or after the saline rinsing process before the blood treatment. Initiation of the pressure-holding test can be made dependent upon various criteria, for example, only when there is a positive dialysis fluid pressure.

The sections of the lines connected to the dialyzer on the dialyzer end can be separated by shut-off devices. Such shut-off devices are present anyway in the known dialysis machines. Thus, the flow path through the blood outlet line can be interrupted with the venous shut-off clamp, for example. With the known dialysis machines, which have a volumetric balancing chamber, shut-off devices are also provided in the dialysis fluid inlet and outlet lines. For example, the valves at the inlet and outlet ends of the balancing chamber halves of the balancing device may be used for interrupting the flow path. These valves which are switched in alternation permit a pressure-holding test even while dialysis fluid is flowing through the dialyzer.

A separate ultrafiltration device with these machines is stopped and also tested for leakage over the part on the dialyzer end. The advantage of the method according to the present invention and the device according to the present invention is that it is possible to perform leakage tests on the blood lines between the blood pump and the venous shut-off clamp, the dialyzer and its hose couplings, and the dialysis fluid lines including any balancing and ultrafiltration devices that might be present. It is also advantageous that the mechanical function of the venous shut-off clamp and the functioning of the blood pump can be tested simultaneously with the leakage test.

Inadequate functionality of a partial device of the blood treatment machine is advantageously deduced if the pressure drop per unit of time exceeds a predetermined limit value. However, it is also possible to measure the period of time during which the excess pressure drops to a certain value. This period of time is then compared with a given limit value. It is also possible to analyze the deviation of the curve from given curves as a function of time.

The excess pressure in the section of the blood outlet line on the dialyzer end is preferably monitored so that the venous blood pressure sensor, which is present in the known dialysis machines anyway, can be used. In principle, however, any sensor connected to the hydraulic volume to be tested can be used. To this extent, the test pressure can also be monitored with sensors on the dialysate end.

When a great pressure drop is detected, an alarm is preferably delivered. In addition, the required safety procedures can be initiated automatically.

BRIEF DESCRIPTION OF THE FIGURE

One embodiment of a hemodialysis machine with a device for monitoring a partial device thereof is described in greater detail below with reference to.

DETAILED DESCRIPTION

Figure 1:
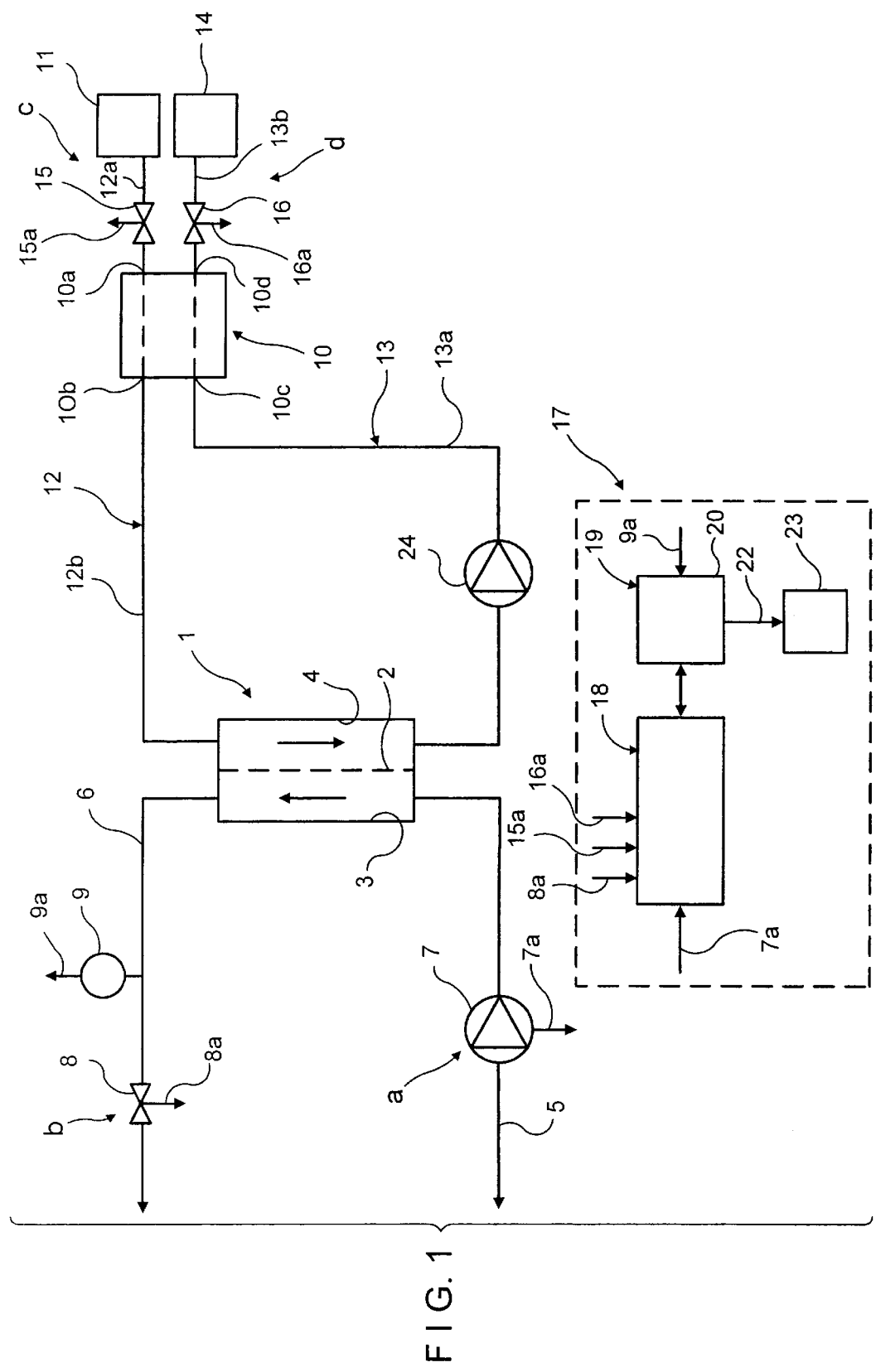
FIG. 1, which illustrates the hemodialysis machine of the present invention in a simplified schematic diagram.

The hemodialysis machine has a dialyzer 1 which is subdivided by a semipermeable membrane 2 into a blood chamber 3 and a dialysis fluid chamber 4. A blood inlet line 5 leads to the inlet of the blood chamber 3, while a blood outlet line 6 is connected to the outlet of the blood chamber 3. An occluding blood pump 7, e.g., a roller pump, is connected to blood inlet line 5. The roller pump forms separation point a. An electromagnetically operable venous shut-off clamp 8 is connected to blood outlet line 6 at separation point b. Upstream from the venous shut-off clamp 8, a venous pressure sensor 9 is connected to the blood outlet line for monitoring the pressure in the line.

The hemodialysis machine has a device 10 for balancing the dialysis fluid coming into dialyzer 1 against the dialysis fluid coming out of the dialyzer and for sampling a predetermined amount of ultrafiltrate. FIG. 1 gives only the outlines of the balancing and ultrafiltration device 10, which is described in more detail in German Patent Application No. 42 39 937 A, for example, which is hereby incorporated by reference herein. The balancing and ultrafiltration device is represented here by an equivalent circuit diagram with a first inlet 10a and outlet 10b for connection of a dialysis fluid inlet line and a second inlet 10c and outlet 10d for connection of a dialysis fluid outlet line.

The device for supplying dialysis fluid 11 is connected to the first inlet 10a of the balancing and ultrafiltration device 10 by a first section 12a of the dialysis fluid inlet line 12, and its first outlet 10b is connected to the inlet of the dialysis fluid chamber 4 of the dialyzer 1 by a second section 12b of the dialysis fluid inlet line. The outlet of the dialysis fluid chamber 4 of dialyzer 1 is connected to the second inlet 10c of the balancing and ultrafiltration device 10 by a first section 13a of dialysis fluid outlet line 13b and its second outlet 10d is connected to a discharge point or outlet 14 by the second section 13b of the dialysis fluid outlet line. A dialysis fluid pump 24 is connected to the first section 13a of dialysis fluid outlet line 13.

A second electromagnetically operable shut-off clamp 15 is connected to the first section 12a of dialysis fluid inlet line 12, and a third electromagnetically operable shut-off clamp 16 is connected to the second section 13b of dialysis fluid outlet line 13. The second and third shut-off clamps 15 and 16, which are arranged at separation point c downstream from dialysis fluid source 11 or at separation point d upstream from discharge point 14, may also be part of the balancing and ultrafiltration device 10. The known balancing and ultrafiltration devices, which work with a volumetric balancing chamber, already have such shut-off devices with which the flow path through the dialysis fluid inlet and outlet lines can be interrupted. For the sake of simplicity, however, the second and third shut-off clamps 15, 16 are shown in the figure as parts separate from the balancing and ultrafiltration device.

The hemodialysis machine has a device 17 for monitoring the functionality of a partial device thereof, comprising a control device 18 and a pressure measuring device 19.

Control device 18 is connected by control lines 8a, 15a, 16a to shut-off clamps 8, 15, 16 for control thereof. Control device 18 is connected by another control line 7a to blood pump 7 for controlling the latter. The measured values of venous pressure sensor 9 are transmitted over a data line 9a to a comparator 20 which is connected by a control line 21 to control device 18. Comparator 20 is connected by another control line 22 to an acoustic and/or optical alarm device 23.

During operation of the hemodialysis machine, the patient's blood flows through blood inlet line 5 into blood chamber 3 of dialyzer 1 and through blood outlet line 6 back to the patient, while the dialysis fluid flows through dialysis fluid inlet line 12 into the dialysis fluid chamber 4 of dialyzer 1 and out of the dialysis fluid chamber into discharge point 14 through the dialysis fluid outlet line 13.

To check the functionality of the partial device of the hemodialysis machine, control device 18 first closes the three shut-off devices 8, 15, 16. Blood pump 7 is operated by control device 18 until a certain excess pressure has built up in the closed volume including dialyzer 1 and the sections of the dialysis fluid inlet and outlet lines and the blood inlet and outlet lines on the dialyzer end. The excess pressure established in the closed volume is monitored with venous pressure sensor 9 and is compared with a predetermined limit value in comparator 20. When the excess pressure reaches the predetermined limit value, control device 18 shuts down blood pump 7. Due to the excess pressure in blood chamber 3 of dialyzer 1, ultrafiltrate passes through its membrane 2 into dialysis fluid chamber 4, thereby generating the test pressure on the dialysate side. The excess pressure is then monitored with venous pressure sensor 9, with the pressure drip being detected per unit of time. After a certain period of time has elapsed, the excess pressure is measured with venous pressure sensor 9, and the output signal of pressure sensor 9 is compared with a predetermined limit value in comparator 20. If the excess pressure is below the limit value, comparator 20 controls the acoustic and/or optical alarm device 23 so that any leakage in the system can be detected immediately and the required safety measures can be initiated.

In the event that the excess pressure does not drop below the predetermined limit value, control device 18 opens shut-off clamps 8, 15, 16 again and starts operation of blood pump 7 again. For controlled reduction of the test pressure, it may be necessary to activate the ultrafiltration device briefly.

The functionality test can be performed at certain intervals. However, it is also possible to perform just one test before the actual dialysis treatment.

What is claimed is:

1. A method for monitoring a part of a blood treatment machine, the blood treatment machine having a dialyzer subdivided by a semipermeable membrane into a first chamber having a first chamber inlet and a first chamber outlet and a second chamber having a second chamber inlet and a second chamber outlet; a blood inlet line connected to the first chamber inlet and to a blood pump; a blood outlet line connected to the first chamber outlet; a dialysis fluid inlet line leading from a dialysis fluid source to the second chamber inlet; and a dialysis fluid outlet line leading from the second chamber outlet to a discharge point, the method comprising:

separating the dialysis fluid inlet line at a first separation point, the dialysis fluid inlet line having a dialysis fluid inlet section between the dialyzer and the first separation point;

separating the dialysis fluid outlet line at a second separation point, the dialysis fluid outlet line having a dialysis fluid outlet section between the dialyzer and the second separation point;

separating the blood outlet line at a third separation point, the blood outlet line having a blood outlet line section between the dialyzer and the third separation point;

separating the blood inlet line at a fourth separation point, the blood inlet line having a blood inlet line section between the dialyzer and the fourth separation point;

building up an excess pressure in a closed system, the closed system including the dialyzer, the dialysis fluid inlet section, the dialysis fluid outlet section, the blood outlet line section and the blood inlet line section; and monitoring the excess pressure to detect a pressure drop in the closed system.

2. The method according to claim 1 wherein the blood pump is an occluding pump forming the fourth separation point, the blood pump operating to build up the excess pressure after the separating of the dialysis fluid inlet and outlet lines and the blood outlet line.

3. The method according to claim 2 wherein the blood pump operates until a predetermined excess pressure has built up in the closed system.

4. The method according to claim 1 wherein the blood pump is an occluding pump forming the fourth separation point, the blood pump operating before the separating of the blood outlet line and being stopped at the separating of the blood outlet line.

5. The method according to claim 1 further comprising determining a lack of functionality if a pressure drop per unit of time is greater than a predetermined limit value.

6. The method according to claim 1 further comprising monitoring the excess pressure in the blood outlet line section.

7. The method according to claim 1 wherein the separating of the dialysis fluid inlet and outlet lines occurs when the blood inlet and outlet lines and the first chamber are filled with blood during operation of the blood treatment machine, and the dialysis fluid inlet and outlet lines and the second chamber are filled with dialysis fluid.

8. A blood treatment machine comprising:
a dialyzer subdivided by a semipermeable membrane into a first chamber having a first chamber inlet and a first chamber outlet and a second chamber having a second chamber inlet and a second chamber outlet;
a blood inlet line connected to the first chamber inlet and to a blood pump and having a blood inlet line section between the first chamber inlet and the blood pump;

a blood outlet line connected to the first chamber outlet and to a first shut-off device and having a blood outlet line section between the first chamber outlet and the first shut-off device;

a dialysis fluid inlet line leading from a dialysis fluid source to the second chamber inlet, the dialysis fluid inlet line being connected to a second shut-off device and having a dialysis fluid inlet line section between the second chamber inlet and the second shut-off device;

a dialysis fluid outlet line leading from the second chamber outlet to a machine outlet, the dialysis fluid outlet line being connected to a third shut-off device and having a dialysis fluid outlet line section between the second chamber outlet and the third shut-off device; and a monitoring device for monitoring functionality of a part of the machine, the monitoring device including:

a control device for actuating the first, second and third shut-off devices and for controlling the blood pump to build up an excess pressure in a closed volume containing the dialyzer, the dialysis fluid inlet and outlet line sections and the blood inlet and outlet line sections; and a pressure-measuring device for detecting a pressure drop in the closed volume.

9. The device according to claim 8 wherein the pressure-measuring device has a pressure sensor and a comparator for comparing an output signal of the pressure sensor with a predetermined limit value.

10. The device according to claim 9 wherein the pressure sensor is arranged in the blood outlet line section.

11. The device according to claim 8 wherein the control device is capable of shutting down the blood pump after a predetermined excess pressure forms in the closed volume.

12. The device according to claim 8 wherein the monitoring device further includes an alarm device for delivering an acoustic and/or optical alarm when a pressure drop is detected in the closed volume.

* * * * *

UNITED STATES PATENT AND TRADEMARK OFFICE
CERTIFICATE OF CORRECTION

PATENT No. : 6,066,261

DATED : May 23, 2000

INVENTOR(S): Reiner SPICKERMANN

It is certified that error appears in the above-identified patent and that said Letters Patent is hereby corrected as shown below:

Column 1, line 57, "partial device" should be changed to -- part --.

Column 2, line 44, "partial device" should be changed to -- part --.

Column 4, line 8, "partial device" should be changed to -- part --.

Column 5, line 45, change "drip" to -- drop --.

Signed and Sealed this

Fifteenth Day of May, 2001

*Attest:*

NICHOLAS P. GODICI

*Attesting Officer*   Acting Director of the United States Patent and Trademark Office